Figure 1:

United States Patent [19]
Garry, Jr.

[11] Patent Number: 5,580,772
[45] Date of Patent: Dec. 3, 1996

[54] ASSOCIATION BETWEEN A NOVEL HUMAN INTRACISTERNAL A-TYPE RETROVIRAL PARTICLE-TYPE II (HIAP-II) AND IDIOPATHIC CD4+ T-LYMPHOCYTOPENIA (ICL)

[75] Inventor: Robert F. Garry, Jr., New Orleans, La.

[73] Assignee: The Administrattors of the Tulane Educational Fund, New Orleans, La.

[21] Appl. No.: 245,385

[22] Filed: May 17, 1994

[51] Int. Cl.$^6$ ............... C12N 7/00; C12N 7/02; A61K 39/21
[52] U.S. Cl. ............ 435/235.1; 435/5; 435/239; 424/207.1
[58] Field of Search ............... 435/235.1, 239, 435/5; 424/207.1, 208.1

[56] References Cited

U.S. PATENT DOCUMENTS

| | | | |
|---|---|---|---|
| 5,344,774 | 9/1994 | Garry, Jr. et al. | 435/235.1 |
| 5,364,757 | 11/1994 | Garry, Jr. et al. | 435/5 |

FOREIGN PATENT DOCUMENTS

| | | | |
|---|---|---|---|
| WO91/18089 | 11/1991 | WIPO | C12N 7/00 |
| WO93/12221 | 6/1993 | WIPO | C12N 7/02 |

OTHER PUBLICATIONS

Ascher et al., 1988, AIDS as Immune System Activation: A Model for Pathogenesis, Clin. Exp. Immunol. 73:165–167.
Barré–Sinoussi et al., 1983, Isolation of a T–Lymphotropic Retrovirus from a Patient at Risk for Acquired Immune Deficiency Syndrome (AIDS), Science 220:868–871.
Belkin et al., 1982, Lack of Type C Virus Antibodies In Systemic Lupus Erythematosous, J. Rheumatol. 9:613–616.
Castro et al., 1992, Kaposi's Sarcoma and Disseminated Tuberculosis in HIV–Negative Individual, Lancet 339:868.
CDC 1992, Unexplained CD4+ T–Lmphocyte Depletion in Persons Without Evident HIV Infection—United States, MMWR 41:541–45.
CDC 1992, Update: CD4+ T–Lymphocytopenia in Persons Without Evident HIV Infection—United States, MMWR 41:578–79.
Cozon et al., 1990, Profound CD4+ Lymphocytopenia in the Absence of HIV Infection in a Patient With Visceral Leishmaniasis, N., Eng. J. Med. 322:132.
Datta et al., 1978, Genetic Studies of Autoimmunity and Retrovirus Expression in Crosses of New Zealand Black Mice, J. Exp. Med. 147:854–871.
Datta et al., 1978, Genetic Studies of Autoimmunity and Retrovirus Expression in Crosses of New Zealand Black Mice, J. Exp. Med. 147:872–881.
Datta et al., 1982, Analysis of Recombinant Inbred Lines Derived from "Autoimmune" (NZB) and High Leukemia(C58) Strains: Independent Multigenic Systems Control B Cell Hyperactivity, Retrovirus Expression, and Autoimmunity, J. Immunol. 129(4):1539–1544.
Daus et al., 1989, Reduced CD4+ Count, Infections, and Immune Thrombocytopenia Without HIV Infection, Lancet 2:559–60.

Djomand et al., 1994, Idiopathic CD4+ T–Lymphocyte Depletion in a West African Population, AIDs 8:843–47.
Duncan et al., 1993, Idipathic CD4+ T–Lymphocytopenia—Four Patients with Opportunistic Infections and No Evidence of HIV Infection, N. Eng. J. Med. 328:393–398.
Etkin et al., 1989 Detection and Analysis of Antibodies Against Retrovirus Determinants in the Sera of Haematologic Patients, Acta Virol. 33:151–161.
Fauci, 1993, CD4+ T–Lymphocytopenia Without HIV Infection—No Lights, No Camera, Just Facts, N. Eng. J. Med. 328:429–31.
Garry et al., 1988, Documentation of an AIDS Virus Infection in the United States in 1968, JAMA 260(14):2085–2087.
Garry et al., 1990, Detection of a Human Intracisternal A–Type Retroviral Particle Antigenically Related to HIV, Science 250:1127–1129.
Gatenby, 1989, Reduced CD4+ T Cells and Candidiasis in Absence of HIV Infection, Lancet 1:1027–28.
Gupta et al., 1992, Detection of a Human Intracisternal Retroviral Particle Associated with CD4+ T—cell Deficiency, PNAS, USA 89:7831–35.
Hart et al., 1979, Viruses and Lymphocytes in Rheumatoid Arthritis, II. Examination of Lymphocytes and Sera from Patients with Rheumatoid Arthritis for Evidence of Retrovirus Infection, Annals of the Rheumatic Diseases 38:514–525.
Heredia et al., 1994, Absence of Evidence of Retroviral Infection in Idiopathic CD4+ T–Lymphocytopenia Syndrome, AIDS 8:267–68.
Ho et al., 1993, Idiopathic CD4+ T–Lymphocytopenia—Immundeficiency Without Evidence of HIV Infection, N. Eng. J. Med. 328:380–385.
Kam–Hansen et al., 1989, Retrovirus in Multiple Sclerosis, Acta Neurol, Scand. 80:467–471.
Kelley et al., 1981, Prostaglandin $E_1$ Inhibits T–Cell Proliferation and Renal Disease in MRL/1 Mice, Clin. Immunool. Immunopath. 21:190–203.
Laurence et al., 1992, Acquired Immunodeficiency Without Evidence of Infection with Human Immunodeficiency Virus Types 1 and 2, Lancet 340:273–274.
Laurence, 1993, T–Cell Subsets in Health, Infectious Disease, and Paropathic CD4+ T Lymphocytopenia, Ann. Int. Med. 119:55–62.

(List continued on next page.)

*Primary Examiner*—Mary E. Mosher
*Attorney, Agent, or Firm*—Pennie & Edmonds

[57] ABSTRACT

The present invention relates to the discovery of a novel retroviral particle associated with idiopathic CD4+ T-lymphocytopenia (ICL). New methods of diagnosis and treatment of ICL, novel cell lines comprising the new retrovirus, assay systems that may be used in the development of antiretroviral pharmaceuticals, model systems for the study of ICL and other immune diseases including acquired immunodeficiency syndrome (AIDS), and a diagnostic kit are provided by the present invention.

5 Claims, 6 Drawing Sheets

OTHER PUBLICATIONS

Leiter et al., 1986, Glucose Induces Intracisternal Type A Retroviral Gene Transcription and Translation in Pancreatic Beta Cells, J. Exp. Med. 163:87–100.

Lueders and Kuff, 1979, Genetic Individuality of Intracisternal A–Particles of *Mus musculus,* J. Virol. 30:225–231.

Maeda et al., 1985, Serum Antibody Reacting with Placental Syncytiotrophoblast in Sera of Patients with Autoimmune Diseases—A Possible Relation to Type C RNA Retrovirus, Clin. Exp. Immunol. 60:645–653.

Montella et al., 1994, CD4+ T–Lymphocytopenia and Severe Infections in an HIV–Negative Ethiopian Man, AIDS 8:390–391.

Oldstone et al., 1976, Autologous Immune Responses to the Major Oncornavirus Polypeptides in Unmanipulated AKR/J Mice, J. Virology 18(1):176–181.

Ono et al., 1985, Human Thymus Retrovirus—Is Human Thymus Retrovirus a Pathogenic Virus for Human Autoimmune Diseases?, Keio J. Med. 34:1–16.

Ono et al., 1986, *In Vitro* Transmission of Retrovirus–like Particles Detected in Human Thymus Cells, in Abstracts of 14th International Cancer Congress, Budapest, Hungary Aug. 12–27, vol. 2, p. 626, Abstract No. 2394.

Pankhurst and Peakman, 1989, Reduced CD4+ T Cells and Severe Oral Candidasis in Absence of HIV Infection, Lancet 1:672.

Query and Keene, 1987, A Human Autoimmune Protein Associated with U1 RNA Contains a Region of Homology That Is Cross–Reactive with Retroviral p30$^{gag}$ Antigen, Cell 51:211–220.

Rucheton et al., 1985, Presence of Circulating Antibodies Against gag–Gene MuLV Proteins in Patients with Autoimmune Connective Tissue Disorders, Virology 144:468–480.

Rucheton et al., 1987, Human Autoimmune Serum Antibodies Against Gag Gene P30 Retroviral Protein Also React with a U1–SnRNP 66K Comigrant Protein, Biol. of the Cell 60:71–72.

Seligmann et al., 1991, CD4+ Lymphocytopenia Without HIV in Patient with Cryptococcal Disease, Lancet 337:57–58.

Smith et al., 1993, Unexplained Opportunistic Infections and CD4+ T–Lymphocytopenia Without HIV Infection, N. eng. J. Med. 328(6):373–379.

Soriano et al., 1992, Idiopathic CD4+ T–Lymphocytopenia, Lancet 340:607–8.

Spira et al., 1993, Idiopathic CD4+ T–Lymphocytopenia—An Analysis of Five Patients with Unexplained Opportunistic Infections, N. Eng. J. Med. 328:386–392.

Suni et al., 1981, Retrovirus p30–Related Antigen in Human Syncytiotrophoblasts and IgG Antibodies in Cord–Blood Sera, Int. J. Cancer 28:559–566.

Talal and Steinberg, 1974, The Pathogenesis of Autoimmunity in New Zealand Black Mice, Curr. Topics Microbiol. Immunol. 64:79–103.

Talal et al., 1990, Sjogren's Syndrome: Dection of Antibodies to Retroviral Proteins in Patient Sera and Isolation of an A–Type Retrovirus Following Exposure of Lymphoblastoid Cells to Patient Biopsy Material, Faseb J. 4:A2102, Abstract No. 2369.

Talal et al., 1990, Detection of Serum Antibodies to Retroviral Proteins in Patients with Primary Sjorgen's Syndrome (Autoimmune Exocrinopathy), Arthritis and Rheumatism 33:774–781.

Talal et al., 1990, A Conserved Idiotype and Antibodies to Retroviral Proteins in Systemic Lupus Erythematosus, J. Clin. Invest. 85:1866–1871.

The Merck Index, 11th Ed. 1989, p. 490, entry 3092.

The Merck Index, 11th Ed. 1989, p. 1597, entry 10023.

Yang and Wivel, 1973, Analysis of High–Molecular–Weight Ribonucleic Acid Associated with Intracisternal A Particles, J. Virol. 11:287–298.

Ziegler and Stites, 1986, Hypothesis: AIDS is an Autoimmune Disease Directed at the Immune System and Triggered by a Lymphotropic Retrovirus, Clin. Immunol. Immunopath. 41:305–313.

ASSOCIATION BETWEEN A NOVEL HUMAN INTRACISTERNAL A-TYPE RETROVIRAL PARTICLE-TYPE II (HIAP-II) AND IDIOPATHIC CD4+ T-LYMPHOCYTOPENIA (ICL)

TABLE OF CONTENTS

1. Field of the Invention
2. Background of the Invention
3. Summary of the Invention
4. Description of the Figures
5. Detailed Description of the Invention
6. Example: ICL: Initial Characterization of a Novel Human Intracisternal A-Type Retroviral Particle Type-II Present In Lymphoblastoid Cells Co-Cultured With Peripheral Blood Mononuclear Cells
   6.1. Cell Culture
   6.2. Electron Microscopy
   6.3. Retrovirus Purification And Western Blotting
7. Deposit Of Biological Materials

1. FIELD OF THE INVENTION

The present invention relates to the discovery of a novel retroviral particle associated with idiopathic CD4+ T-lymphocytopenia in humans. New therapeutic and diagnostic methods, novel cell lines comprising the new retrovirus, assay systems that may be used in the development of anti-retroviral pharmaceuticals, and model systems for the study of idiopathic CD4+ T-lymphocytopenia are provided by the present invention.

2. BACKGROUND OF THE INVENTION

Idiopathic CD4+ T-lymphocytopenia (ICL) is a newly described immunodeficiency syndrome in which human immunodeficiency virus (HIV), the causative agent of acquired immune deficiency syndrome (AIDS), can not be detected (Laurence et al., 1992, *Lancet* 340: 273–74; CDC 1992, *MMWR* 41: 541–45; CDC 1992, *MMWR* 41: 578–79; Duncan et al., 1993, *NEJM* 328: 393–98; Ho et al., 1993, *NEJM* 328: 373–79; Spira et al., 1993, *NEJM* 328: 386–92). A definition of ICL by the Centers for Disease Prevention and Control (CDC) includes the repeated measurement of fewer than 300 CD4 cells/µl in peripheral blood and repeated lack of seropositivity for human immunodeficiency virus (HIV), types I or II, or human T-lymphotropic virus (HTLV), types I or II. While some ICL patients belong to some of the same risk groups, such as male homosexuals, transfusion recipients, and intravenous drug abusers in which AIDS was first detected, a majority of patients do not belong to any risk group for HIV. As in AIDS, ICL patients have reduced numbers of CD4+ T-lymphocytes and many have developed the opportunistic infections or otherwise rare cancers associated with AIDS. Some ICL patients have died as a result of their immunodeficiency.

Although some aspects of this immunodeficiency resemble AIDS, HIV can not be detected in ICL patients. Confirmed ICL patients have proven to be negative for DNA sequences of HIV and HTLV by polymerase chain reaction (PCR) (Ho et al., supra; spira et al., supra). The causes of ICL are not known, and except for repeated CD4 quantitations there are no known methods for diagnosis of ICL.

In previous studies of autoimmune diseases, a human intracisternal A-type retroviral particle (HIAP-I) was identified in patients with Sjögren's Syndrome (SS), a systemic autoimmune disease (U.S. patent application Ser. No. 07/526,349 filed May 21, 1990 (Garry I); and also Garry et al., 1990, *Science* 250: 1127–29 (Garry II)). Another group recently described an intracisternal retroviral particle, designated "human intracisternal retroviral particle" (HICRV), in lymphoblastoid cells co-cultured with peripheral blood mononuclear cells from a 66-year old female patient with a history of *Pneumocystis carinii* pneumonia (PcP) (Gupta et al., 1992, *PNAS* 89: 7831–35). HICRV appears similar to HIAP-I, and is likely to represent a second isolation of that retrovirus.

3. SUMMARY OF THE INVENTION

The present invention relates to purified preparations of a novel retrovirus associated with idiopathic CD4+ T-lymphocytopenia (ICL), and with diagnostic and therapeutic methods, novel cell lines, and assay and model systems for the study of ICL. It is based, at least in part, on the discovery of a novel retrovirus, HIAP-II, which is antigenically similar to HIAP-I, and which has a protein, p97, that appears to contain an epitope that is cross-reactive with HIAP-I, and in some cases with an HIV protein.

According to the present invention, a diagnosis of ICL in a majority of patients may be supported, and its clinical course may be monitored, by demonstrating the presence of anti-HIAP-II antibodies and/or measuring the levels of such antibodies. In preferred embodiments of the invention, antibodies that recognize a 97,000 dalton protein of the retrovirus of the invention are detected and/or measured. Alternatively, ICL may be diagnosed or monitored by directly or indirectly demonstrating HIAP-II viral particles in the cells of a patient.

In additional embodiments, the present invention provides for assay systems that may be used in the development of anti-HIAP-II pharmaceuticals, as well as for model systems for ICL.

In additional embodiments, diagnostic kits are provided to detect and quantitate antibodies directed to inactivated HIAP-II viral particles or HIAP-II proteins in body fluids or tissues of patients.

Furthermore, according to the invention, patients suffering from ICL who have been found to exhibit the novel retrovirus of the invention or anti-HIAP-II antibodies may be treated with agents known to be useful in the treatment of retroviral diseases, including, but not limited to, agents which interfere with reverse transcriptase function, such as, for example, nucleoside analogues (e.g., AZT, dideoxycytosine (ddC), and dideoxyinosine (ddI)), non-nucleoside inhibitors, and antisense oligonucleotides.

4. DESCRIPTION OF THE FIGURES

FIG. 1. Electron micrograph of intracisternal A-type retroviral particles-Type II (HIAP-II) in RH9/CB cells. RH9 cells co-cultured with peripheral blood mononuclear cells (PBMC) from a New Orleans ICL patient underwent a round of significant cell killing within one week following culture initiation. After one month in culture, surviving cells, including syncytial cells, were fixed and embedded according to methods described previously (Garry II), and examined by electron microscopy. The diameters of the two budded intracisternal particles are approximately 60 nm.

Figure 2A:
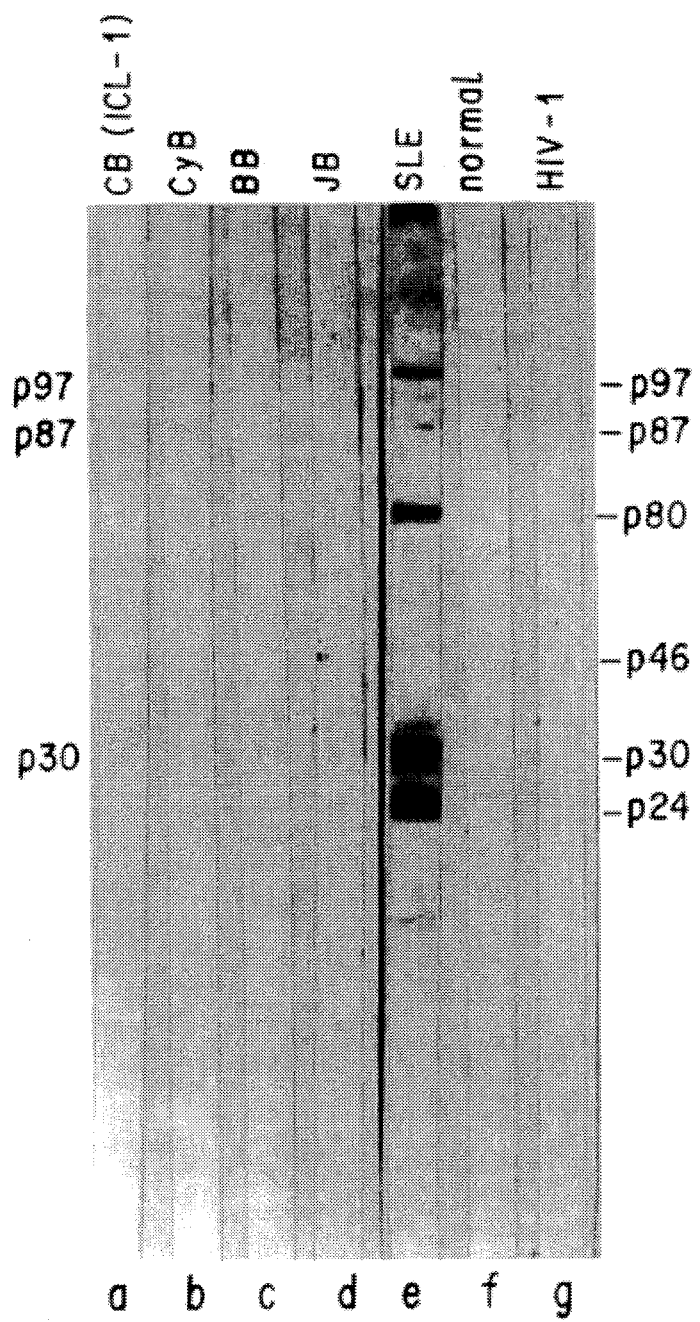
Figure 2B:
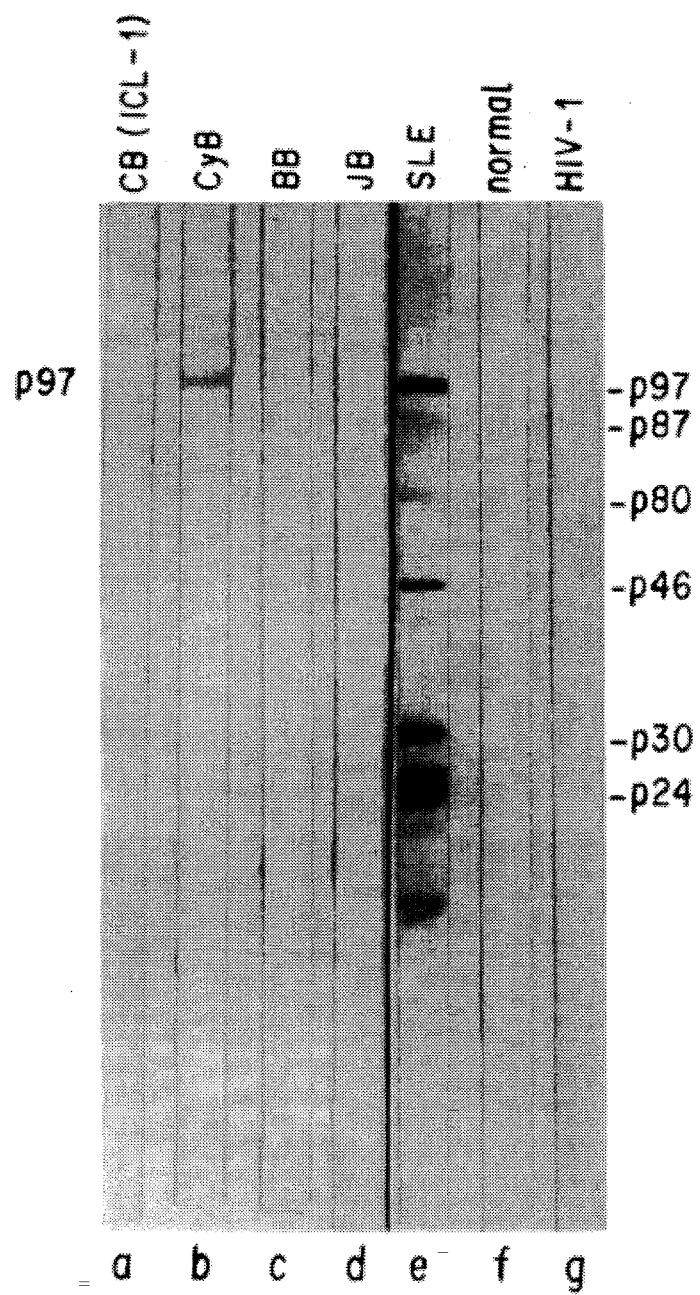
Figure 2C:
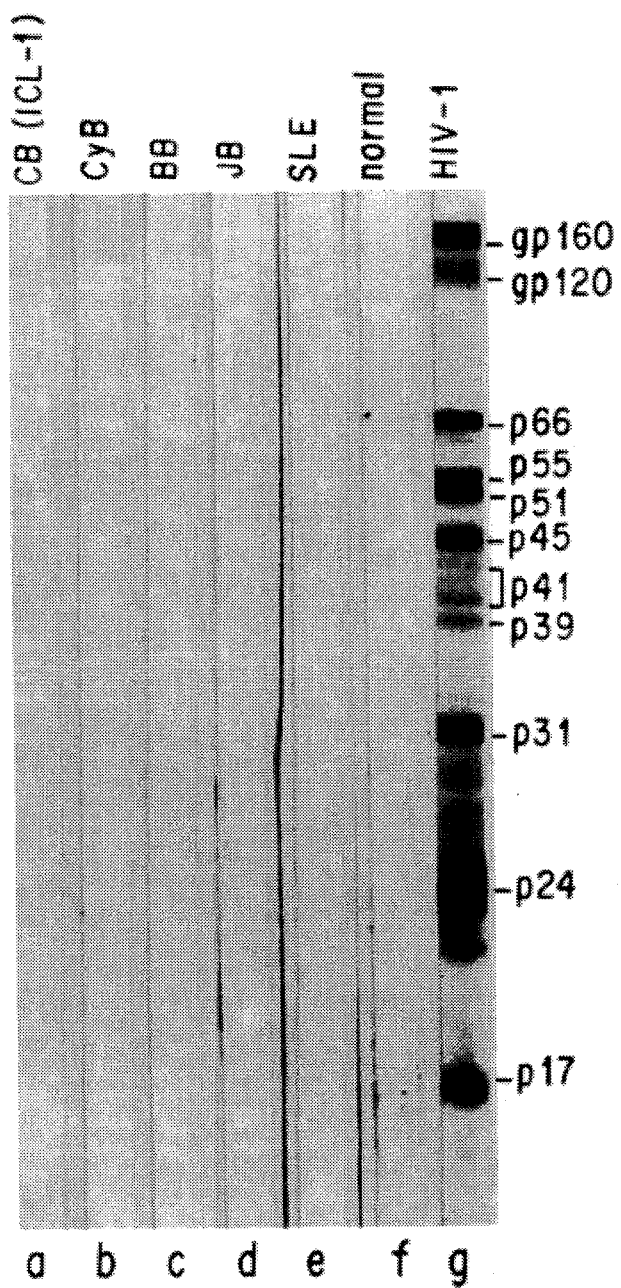

FIGS. 2 (A–C). Western immunoblot analysis of serum antibodies. FIG. 2A. Reaction of sera with proteins from HIAP-II. FIG. 2B. Reaction of sera with proteins from HIAP-I, a retrovirus associated with Sjögren's Syndrome. FIG. 2C. Reaction of sera with proteins from HIV-1. Sera from New Orleans ICL patient (CB; lane a); members of patient CB's family (CyB, BB, JB; lanes b–d); a patient suffering from an autoimmune disease (systemic lupus erythematosus, (SLE; lane e)); a control (normal; lane f); and a patient infected with HIV-1 (HIV-1; lane g).

Figure 3A:
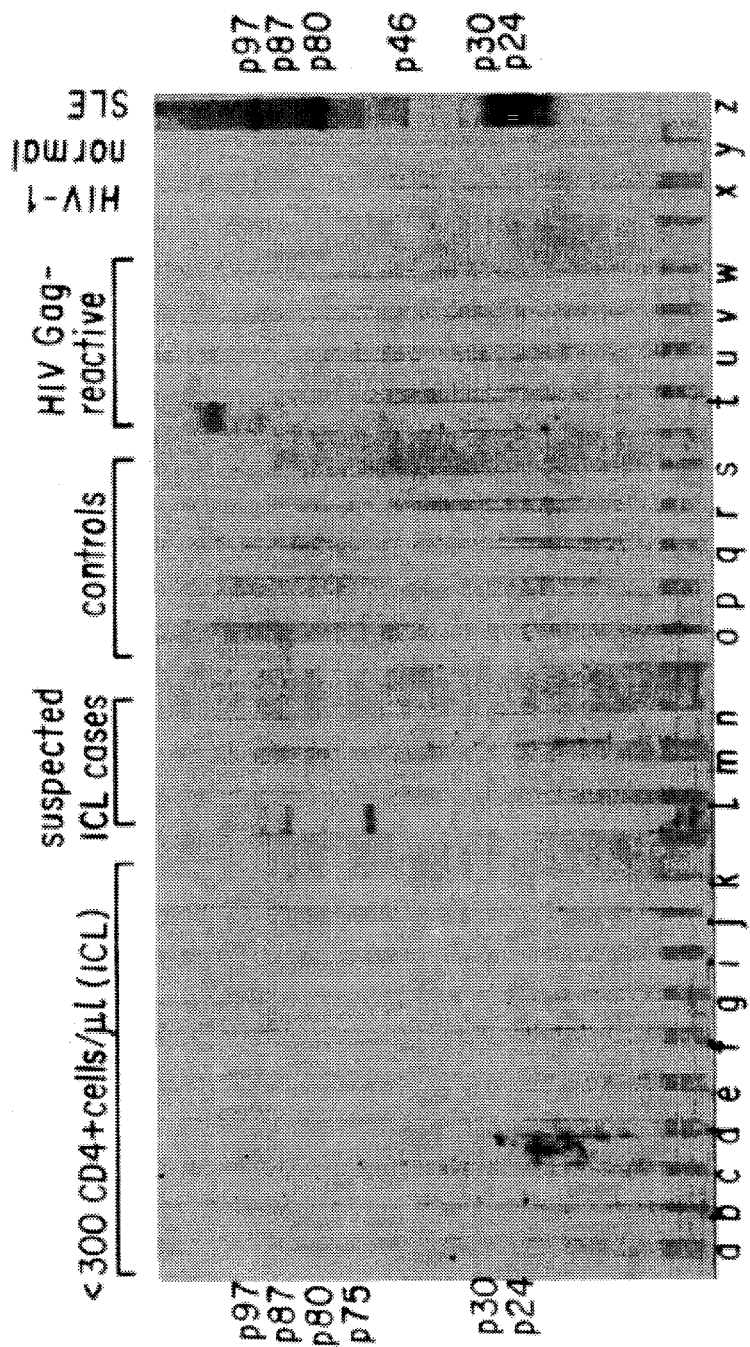
Figure 3B:
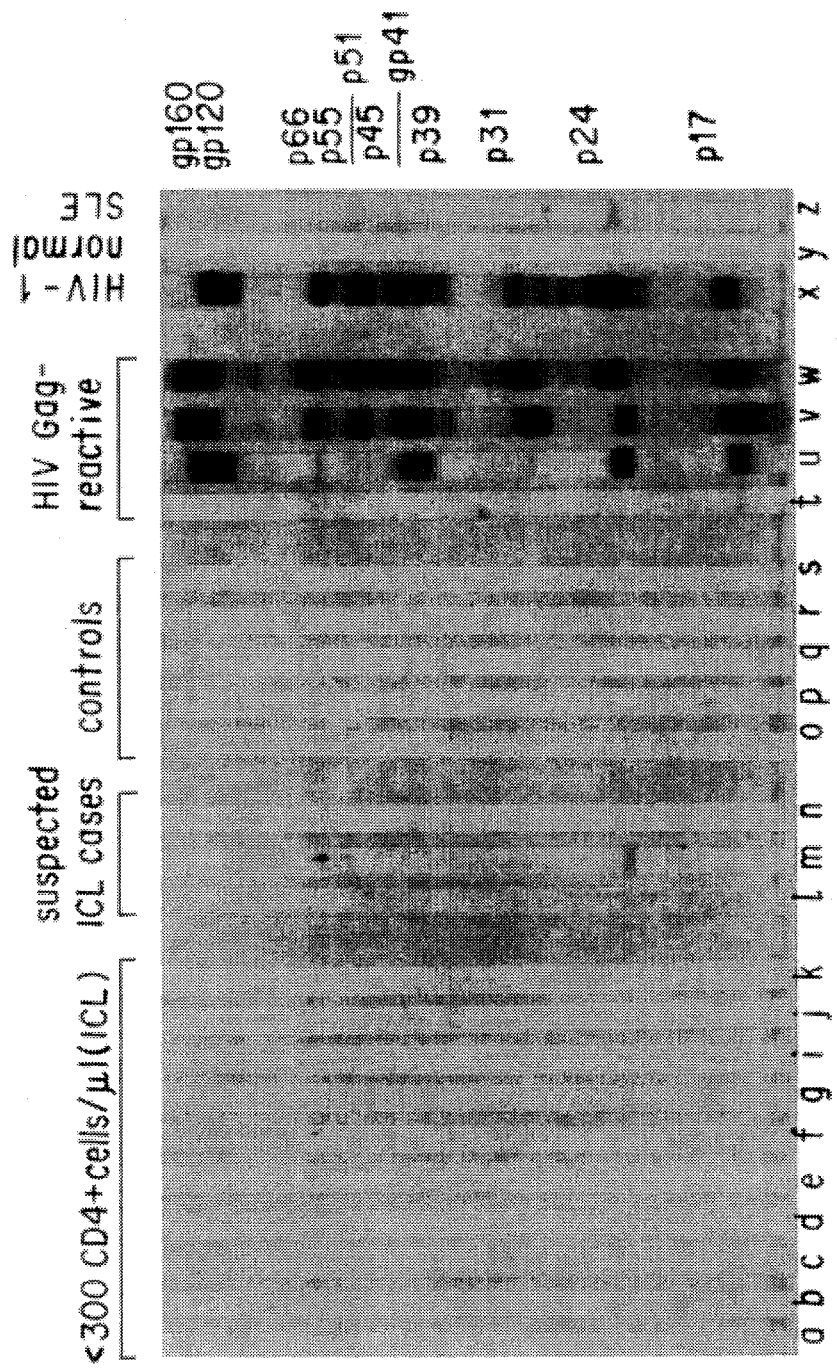

FIGS. 3(A–B). Western immunoblot analysis of serum antibodies. FIG. 3A. HIAP-II protein immunoblots. FIG. 3B. HIV-1 protein immunoblots. Sera from ICL patients (lanes a–k); suspected ICL patients (lanes 1–n); control subjects (lanes o–s, y); patients reactive with HIV-1 proteins (lanes t–x); and a patient with SLE (lane z).

5. DETAILED DESCRIPTION OF THE INVENTION

We have isolated a novel human intracisternal A-type retrovirus, designated HIAP-II, from an ICL patient from New Orleans (patient CB). As observed by electron microscopy, HIAP-II retroviral particles resemble HIAP-I particle in terms of intracellular location. However, HIAP-II particles differ significantly from HIAP-I particles in terms of shape and size.

Preparations of HIAP-II were used to develop a Western immunoblot assay for serum antibodies to this newly identified human retrovirus. Serum antibodies from patient CB reacted to two proteins, p97 and p30, from HIAP-II. The HIAP-II immunoassay was successfully used in a blinded screen of a panel of ICL patient sera to identify a majority (8/13) of confirmed ICL patients without false positive results. These ICL patients produced serum antibodies that react to the 97 Kd protein, or to two or more other bands of 87, 80, 61, 46, 30 or 24 Kd on immunoblots prepared with proteins from HIAP-II isolated from the New Orleans ICL case. These results indicate an association between HIAP-II and ICL, and suggest a possible etiological role for HIAP-II in a substantial majority of ICL patients. In addition, sera from a majority of autoimmune patients reacted to a similar sized (97 Kd) protein in HIAP-II immunoblots, and some (2/10) HIV$^+$(gag-reactive) sera also reacted to this protein.

According to the invention, the novel retrovirus described herein, HIAP-II, may be obtained by co-culturing T-lymphoblastic cells of the RH9 cell line (which is a subclone of H9 cells, which in turn is a subclone of HuT 78 cells, ATCC TIB 161) with peripheral blood mononuclear cells (PBMC) obtained from patients suffering from ICL, according to previously described techniques designed to detect potential infectious agents (Garry II). In a specific embodiment of the invention, blood (5 ml) is obtained from an ICL patient, and PBMCs, or extracts prepared therefrom, are prepared by ficol-hypaque density separation. Purified PBMCs or PBMC extracts from $10^6$ cells are then added to cultures containing $10^7$ RH9 cells.

Once co-culturing of PBMCs and RH9 cells has been initiated, or once extracts from PBMCs have been added to RH9 cell cultures, the cultures are incubated and may be examined from time to time for cell death and the presence of syncytial cells using standard bacteriological techniques. Cell cultures may also be examined for the presence of retrovirus or retroviral antigen using standard virological techniques.

For example, cells, cell supernatants, or lysates of the cell cultures may be examined by electron microscopy for the presence of viral particles. Alternatively, supernatants and lysates may be evaluated by enzyme linked immunosorbent assay (ELISA) techniques utilizing antibodies reactive with retrovirus, or screening may be performed using retrovirus-specific nucleic acid probes in order to identify retroviral nucleic acids. If retrovirus is present, cultures may be expected to screen positive prior to about twelve weeks after addition of PBMCs or PBMC extracts to RH9 cell cultures, although a longer culture period may, in some cases, be necessary. Of note, if cultures are analyzed by electron microscopy, retroviral particles of the invention may be expected to resemble, in terms of intercellular location, but not in terms of shape or size, the human intracisternal A-type particles (HIAP-I) associated with Sjögren's syndrome (SS), a systemic autoimmune disease (See Garry II).

Once evidence of the presence of a retrovirus in culture has been obtained, the retrovirus may be further characterized using methods known in the art to determine its size, molecular biology, etc. For example, and not by way of limitation, cells containing virus may be disrupted in hypotonic buffer, and a microsomal (vesicle) fraction may be prepared which may then be centrifuged at 10,000 g for 10 min. Pelleted material may then be made about 0.1% (v/v) in Triton X-100, layered over a 48% (w/v) sucrose cushion, and centrifuged at 60,000 g for 30 min. Material which pellets through the cushion may then be applied over a 33–68% (w/v) sucrose gradient and centrifuged at 100,000 g for about 12 hours. Fractions from the sucrose gradient may then be assayed for the presence of retroviral related antigens. The retroviral particles of the invention may be detected in the gradient at a density of about 1.2 g/cm$^3$, or in the range of about 1.1 to about 1.4 g/cm$^3$. In this manner, a substantially pure preparation of the retrovirus of the invention, henceforth referred to as HIAP-II (for human intracisternal A-type particle-type II), may be produced.

According to the invention, a diagnosis of an HIAP-II-associated disease in a patient may be supported by testing a sample from the patient for the presence of HIAP-II viral particles, HIAP-II nucleic acids or proteins, or anti-HIAP-II antibodies, in which the presence of such particles, nucleic acids, proteins, or antibodies correlates positively with the presence of disease.

For example, a patient that presents with symptoms and signs consistent with disease that has been characterized as ICL may be tested initially for the presence of anti-retroviral antibodies including, but not limited to, antibodies reactive with antigens such as p24$^{gag}$ from HIV.

In preferred diagnostic methods of the invention, antibodies that recognize a 97,000 dalton protein (p97) of HIAP-II may be detected and/or measured. As exemplified in Section 6, infra, a majority of ICL patients tested produced serum antibodies to p97. Likewise, a majority of autoimmune disease patients tested (including patients suffering from SS, SLE, scleroderma, and juvenile rheumatoid arthritis) produced antibodies toward a similar-sized protein. In addition, only a minority of HIV-1$^+$sera (gag-reactive) reacted to this protein. In most preferred, but non-limiting, embodiments of the invention, detection and/or measurement of levels of such antibodies may be used to support a diagnosis of ICL, but the diagnostic methods of the present invention are not limited to this condition. In order to support a diagnosis of ICL, antibodies directed toward p97, or toward two or more proteins of 87, 80, 61, 46, 30, or 24 Kd, may preferably, but not by way of limitation, occur in a patient who repeatedly shows fewer than 300 CD4 cells/µl of peripheral blood, but is not suffering from an autoimmune disease or from HIV infection.

Antibody detection may be performed utilizing any standard techniques, including ELISA or Western blotting, in which a sample from a patient may be tested for the presence of anti-retroviral antibodies by exposing the serum to immobilized retrovirus or retroviral antigen, and then detecting antibody that has bound to immobilized virus or viral antigen (e.g., by binding of a second, labeled antibody capable of reacting with the antibody adherent to the virus or antigen).

In a specific, nonlimiting embodiment of the invention, Western blotting may be performed as follows: HIAP-II producing RH9/CB cells may be prepared as described in Section 6.1, infra, disrupted in a hypotonic buffer, and used to prepare a microsomal fraction, e.g., by shearing the cells through graded hypodermic needles, pelleting the extract at 10,000 g, making the preparation 0.1% (v/v) in Triton X-100, and layering of lysate over a 48% (w/v) sucrose cushion, followed by centrifugation for 30 min at 60,000 g. The pelleted material may then be collected, applied over a 33–68% (w/v) sucrose gradient, and centrifuged at 100,000 g for about 12 hours. Individual fractions of the gradient may then be loaded into individual wells of a sodium dodecyl sulfate-polyacrylamide slab gel of about a 7–15 percent polyacrylamide gradient, and the proteins in each fraction may be electrophoretically separated, e.g., by electrophoresis at 24 amps (constant current) for about three hours. The resolved proteins in the slab gel may then be transferred to a sheet of nitrocellulose (e.g, by electroblotting using a Transblot (Biorad) apparatus), and then reacted with a reference serum, e.g., from a person suffering from ICL. Antibodies bound to the nitrocellulose sheet may be detected by reacting the sheet sequentially with biotinylated goat anti-human immunoglobulin, avidin coupled to horse radish peroxidase, and nitroblue tetrazolium substrate. Fractions of the gel containing proteins with reactivity to ICL patient serum may be pooled and loaded into a single wide well in a second sodium dodecyl sulfate 7–15 percent polyacrylamide gradient gel, and subjected to electrophoresis at about 24 amps for three hours. The resolved proteins in the slab gel may then be electroblotted to a sheet of nitrocellulose, which may then be reacted with sera from persons suspected of suffering from HIAP-II associated disease. Binding of antibodies may be detected as described supra, or by other standard methods.

Alternatively, substantially pure preparations of p97 protein may be used as binding antigen in standard ELISA type assays. This protein may be prepared, for example, from lysates of HIAP-II producing cell cultures by sodium dodecyl sulfate polyacrylamide gel electrophoresis followed by elution of the appropriate protein band. Such protein, or an antigenic portion thereof, may also be produced by chemical synthesis or recombinant DNA technology.

Furthermore, according to the invention, tissue biopsies, preferably from clinically involved areas, may be tested for the presence of retrovirus or retroviral antigens by in situ binding of anti-HIAP-II antibodies to tissue sections or cells using standard techniques.

In additional embodiments of the invention, the presence of the HIAP-II retrovirus may be detected in cells from a patient, according to the methods set forth supra. In one specific embodiment of the invention, peripheral blood mononuclear cells (PBMCs) may be collected from a patient who is suspected of suffering from ICL, and then tested for the presence of the virus.

A sample from a patient may preferably be a serum sample, but may also be a sample of any body tissue or fluid, including, but not limited to, skin, liver, blood, saliva, urine, cerebrospinal fluid, joint fluid, semen, nasal secretions, etc.

The present invention also provides for a method of supporting a diagnosis of HIAP-II-associated ICL or other disease in a patient comprising detecting HIAP-II nucleic acids in a sample from the patient, in which the presence of HIAP-II nucleic acids correlates positively with a diagnosis of ICL or with another disease. In particular, nonlimiting embodiments of the invention, retroviral nucleic acids may be detected by hybridization techniques. The nucleic acid probe may be ribonucleic acid or deoxyribonucleic acid, and may be labeled with a radioactive isotope, biotin, or any other detectable compound. The hybridization techniques may utilize RNA or DNA prepared from a patient sample, e.g., using Northern blot, Southern blot, or dot blot methods, or may utilize a tissue or cell sample from the patient, e.g., using in situ hybridization methods.

The present invention also provides for diagnostic test kits to support a diagnosis of ICL in patients suspected of suffering from ICL, by detecting and quantitating antibodies directed toward HIAP-II antigens. So, for example, the kit may provide HIAP-II antigens, such as a viral protein of about 97, 87, 80, 61, 46, 30 or 24 Kd expressed by HIAP-II infected cells or tissues. The kit may also provide secondary anti-Ig antibodies with a detectable label, an appropriate diluent for body fluids, and positive and negative controls.

In further embodiments of the invention, determining the presence and amount of HIAP-II retrovirus or anti-HIAP-II retroviral antibodies may be useful in determining the clinical progression of disease, in which case a decline in retrovirus may indicate remission of the disease and/or a positive response to treatment.

The present invention also provides for methods of treating HIAP-II-associated disease, comprising administering to a patient in need of such treatment an effective amount of a compound that is effective in the treatment of retroviral disease, such as an anti-retroviral therapy. In preferred embodiments of the invention, the HIAP-II-associated disease has been categorized as ICL. The association between a retrovirus and ICL presents the possibility that anti-retroviral therapy may be effective in treating some or all patients with the disease. Because evidence indicates that the presence of retrovirus defines a subgroup of ICL patients, it is recommended that anti-retroviral medication be administered only to those patients for whom retroviral infection is clearly determined.

Anti-retroviral therapies include, but are not limited to, administration of an effective amount of a compound or compounds which interfere with the function of reverse transcriptase, including, but not limited to, nucleoside derivatives such as AZT, ddI, ddC, ddT, etc.

The present invention further provides for methods of treatment of an HIAP-II-associated disease, e.g., ICL, comprising administering an effective amount of antisense oligonucleotide that interferes with the transcription or translation of a human retroviral gene to a patient in need of such treatment. Such oligonucleotides may be ribonucleic acid or deoxyribonucleic acid, and may or may not comprise phosphorothioate linkages.

In additional embodiments, antibody directed toward HIAP-II, or a component thereof, that is a polyclonal antibody or a monoclonal antibody, may be administered as treatment to a patient suffering from ICL. Such antibodies may not substantially bind to uninfected human cells or tissue.

In additional embodiments, the substantially purified retrovirus, HIAP-II, of the invention may be used to generate model systems for various diseases including, but not limited to, ICL, autoimmune diseases and AIDS. For example, antibodies directed toward the HIAP-II retrovirus may be induced in laboratory animals which may subsequently be evaluated for immune system phenomena. For example, and not by way of limitation, retrovirus-containing cells generated according to the methods set forth supra may be administered, together with adjuvant, to a primate; standard "booster" doses may subsequently be administered. Animals may then be followed clinically for the appearance of symptoms and signs of immune system diseases, including the sicca syndrome. In addition, tissue biopsies may be studied.

An important feature of the present invention is that it appears that the retrovirus of the invention is related to HIAP-I and, more distantly, to HIV, but that HIAP-II differs in its cytopathicity. The retrovirus of the invention may provide a method for studying the immunological aberrations caused by HIV and HIAP-I which are not due to direct cytopathic effects. Further, inactive formulations of the retrovirus of the invention, or antigenic portions thereof, may be useful in the generation of vaccines against ICL, autoimmune disease, or HIV infection.

The present invention also provides for assay systems that may be used to evaluate the efficacy of compounds toward altering the effects of HIAP-II infection and treating HIAP-II-associated disease. In such assay systems, cells, tissues, or whole organisms that express HIAP-II may be exposed to a test agent and then evaluated to determine the effects of the test agent on the cells, tissues, or organism. Alternatively, cells, tissues, or whole organisms may be exposed to HIAP-II that has previously been exposed to test agent.

Cells that may be utilized in such an assay include, but are not limited to, peripheral blood mononuclear cells (PBMCs), and lymphoid cells, preferably T cell lines.

Tissues that may be utilized include any tissue that comprises cells that are capable of expressing HIAP-II, such as lymph nodes or spleen.

Organisms that may be utilized include single cell or multicellular organisms such as bacteria, yeast, protozoa, nematodes, insects, birds, amphibia, reptiles, or mammals.

The cells, tissues, or organism may then be exposed to an infective concentration of HIAP-II which has been purified or which is not purified but, for example, is in the form of a cell lysate, in order to produce a culture of cells, or a tissue, or an organism that expresses HIAP-II, referred to hereafter as an HIAP-II assay system. For example, a T-lymphocyte HIAP-II assay system may be prepared by adding PBMCs from an ICL patient to a culture of T-lymphocytes, as described supra.

Test agent may then be added to the HIAP-II assay system. Preferably, a number of HIAP-II assay systems may be prepared in parallel and simultaneously administered varying concentrations of test agent. An untreated or sham treated HIAP-II assay system may preferably be used as a control.

Suitable test agents include any compound or combination of compounds which might be suspected of exerting either anti-HIAP-II activity or activity that limits secondary effects of HIAP-II expression. For example, compounds that interfere with the function of reverse transcriptase may be used, including but not limited to AZT, ddI, ddC, ddT, etc. As further examples, antisense oligonucleotides, antibodies, or compounds that have been used to treat autoimmune disease, including immunosuppressive agents such as corticosteroids, imuran, etc., may be evaluated for their effects in the HIAP-II assay system. The present invention accordingly provides for assay systems that may be used in the rational design of compounds that may inhibit any step of viral infection, or any viral component, such as HIAP-II reverse transcriptase or protease.

Parameters that may be measured include any primary or secondary effects of HIAP-II expression, including the number of intracisternal A-type particles, level of reverse transcriptase activity, amount of viral protein (e.g., p97) expressed, level of immune system activation, viral protease activity, lymphokine/cytokine production, cell viability, mitotic activity, spread of HIAP-II infection, cytopathic effects, the level of viral RNA or proviral DNA, etc. In whole organisms, such as laboratory animals, physiological effects including anatomical/histological changes, behavioral changes, alteration in metabolism, renal function, etc., may be measured.

A diminution of an effect of HIAP-II expression resulting from administration of a test agent, relative to the comparable effect of HIAP-II expression measured in an untreated HIAP-II assay system, indicates that the test agent may be useful in the treatment of HIAP-II-mediated disease.

6. EXAMPLE: ICL: INITIAL CHARACTERIZATION OF A NOVEL HUMAN INTRACISTERNAL A-TYPE RETROVIRAL PARTICLE TYPE-II PRESENT IN LYMPHOBLASTOID CELLS CO-CULTURED WITH PERIPHERAL BLOOD MONONUCLEAR CELLS

6.1. Cell Culture

A 40-year old, white male with extremely low CD4 T-cell counts (2% or fewer), and a history of cryptococcal infection, was referred to Tulane Medical School and the Tulane-LSU-Charity General Clinical Research Center. This patient (patient CB), who fits the recently proposed CDC definition of ICL, is married, monogamous, and has no history of drug abuse. However, the patient's wife was a recipient of two units of blood in 1980 during surgery for colon cancer. Peripheral blood mononuclear cells (PBMC) were obtained from patient CB, his wife, and two daughters. PBMCs ($10^6$) from each individual were co-cultured with $10^7$ cells of the RH9 T-lymphoblastic cell line (which is a subclone of H9 cells, which in turn is a subclone of HuT 78 cells, ATCC TIB 161), according to previously described techniques designed to detect potential infectious agents (Garry II).

The cells incubated with PBMCs from patient CB underwent significant cell killing within one week of initiating the co-culture. This was not observed in co-cultures from either the patient's wife or two daughters. The cells that survived this cytopathic effect were grossly similar to uninfected RH9 cells, except that syncytial cells were present in the cultures that were not present in the untreated RH9 cells. These syncytia were not as large as is commonly observed during acute infection with highly cytopathic strains of HIV such as HIV-$1_{LAI}$ (formerly IIIb), but were comparable in size to syncytia that form in cultures of RH9 cells that are persistently infected with HIV-$1_{LA1}$.

6.2. Electron Microscopy

To determine whether a virus could account for the observed cytopathology, the cells (designated RH9/CB) were examined by electron microscopy according to previously described techniques (Garry II) one month after initiating the co-culture with PBMCs from patient CB. The RH9/CB cells were observed to be producing intracisternal A-type retrovirus particles (FIG. 1). These particles resemble, in terms of intracellular location, the intracisternal retroviral particles observed previously in the case of patients with SS, a systemic autoimmune disease (Garry II).

However, the ICL-associated particles (HIAP-II) differed morphologically from HIAP-I in several respects. HIAP-II particles are icosahedral whereas the bulk of particles of HIAP-I are round. The diameter of HIAP-II particles (60 nm) is also smaller than that of HIAP-I particles (70–80 nm).

6.3. Retrovirus Purification And Western Blotting

Patients infected with retroviruses such as HIV and HTLV produce serum antibodies which serve as the basis for tests to determine exposure to the viruses, and as a screen to determine the presence of infectious virus in donated blood prior to transfusion or derivation of blood products. To determine whether ICL patients produce antibodies to HIAP-II, Western immunoblots of HIAP-II proteins were prepared.

HIAP-II from patient CB was propagated in cultures of RH9 cells as described supra. RH9/CB cells producing ICL-associated HIAP-II particles were disrupted in hypotonic buffer (10 mM Tris-HCL, pH 7.4, 1.5 mM $MgCl_2$), and a microsomal (vesicle) fraction was prepared by shearing the cells through a 25-gauge needle and pelleting the extracts at 10,000 g for 10 min. This preparation was made 0.1% (v/v) in Triton X-100, forced through graded hypodermic needles (19–22, and 25-gauge) to shear the vesicles, then layered over a 48% (w/v) sucrose cushion, and pelletted at 60,000 g for 30 min. Material pelleting through the cushion was then applied over a 33–68% (w/v) sucrose gradient and centrifuged at 100,000 g for 12 hr. Fractions corresponding in density to A-type retroviruses (1.1 to 1.4 $g/cm^3$) were pooled.

HIV-$1_{LAI}$ was propagated in RH9 cell cultures, and was partially purified by polyethylene glycol precipitation and gradient centrifugation. HIV-$1_{LAI}$ was inactivated with psoralen and ultraviolet light, detergent disrupted, and purified in a step gradient by standard techniques.

Proteins in the virus preparations were resolved by SDS-PAGE, transferred to nitrocellulose membranes, and the membranes were used to test sera from patient CB, his wife and two daughters, a patient suffering from SLE, a patient infected with HIV-1, and a control.

Serum from patient CB reacted to two proteins, p97 and p30, from the ICL-associated HIAP-II in western immunoblot analysis (FIG. 2A, lane a). This is significant, since fewer than 3% of normal blood donors react to any proteins on these blots (Table I).

TABLE I

Reactivity of serum antibodies of idopathic CD4 T-lymphocytopenia patients to proteins of a human intracisternal A-type retroviral particle type-II

| Subject Group Positive | # positive*/# Tested | % |
| --- | --- | --- |
| <300 CD4+ T-cells/μl | 8/13 | 61.5 |
| suspected ICL patients | 1/7 | 14.3 |
| >300 CD4 T-cells/μl Control subjects (not HIV Gag-reactive) | 0/19 | 0 |

*Reactivity to p97 or to two or more other bands at 1/400 dilution.

Serum from patient CB's wife, CyB, the prior recipient of two blood transfusions, was weakly reactive to several proteins of the ICL-associated HIAP-II preparation (FIG. 2A, lane b). Although not overtly immunodeficient, patient CB's wife had CD4 and total lymphocyte counts in the low normal range (35% CD4+ T-cells; total count 1200). The immunoblot analyses for the patient's two daughters were negative (FIG. 2A, lanes c,d). Serum from the SLE patient reacted strongly with all of the designated HIAP-II proteins (FIG. 2A, lane e). Immunoblot analyses of normal serum (FIG. 2A, lane f), and serum from a patient infected with HIV-1 (FIG. 2A, lane g) were negative.

In immunoblots to HIAP-I proteins, serum from patient CB reacted weakly to p97 (FIG. 2B, lane a), while serum from patient CB's wife, CyB, reacted strongly (FIG. 2B, lane b). The HIAP-I immunoblot analyses for the patient's two daughters were negative (FIG. 2B, lanes c,d). Serum from the SLE patient reacted strongly with all the designated proteins (FIG. 2B, lane e). Immunoblot analyses of normal serum (FIG. 2B, lane f), and serum from a patient infected with HIV-1 (FIG. 2B, lane g) were negative.

In immunoblot analysis with HIV-1 proteins (FIG. 2C), all sera failed to react, except for serum from a patient infected with HIV-1 (FIG. 2C, lane g).

Forty-seven samples of sera were received from the CDC of which 13 were from ICL patients. Approximately half of the ICL patients in this panel were from patients in HIV risk groups, i.e., male homosexuals, intravenous drug abusers, or transfusion recipients. The majority (8/13) of confirmed ICL patients (<300 CD4 T-cells/μl) were identified by Western immunoblot analysis in this blinded screen without false positive results. These eight cases produced serum antibodies that reacted to a 97 Kd protein, or to two or more other bands of 87, 80, 61, 46, 30 or 24 Kd, on immunoblots prepared with proteins from HIAP-II isolated from patient CB, the New Orleans ICL case (FIG. 3A, lanes a–n; Table I).

In immunoblot analysis with HIV-1 proteins, sera from only one of the suspected ICL cases reacted with an HIV-1 protein, p24 (FIG. 3B, lane m). All HIV-sera showed typical reactivities (FIG. 3B, lanes t–x). Control serum was not reactive with HIV-1 proteins (FIG. 3B, lane y). Serum from an SLE patient was reactive towards p24 from HIV-1 (FIG. 3B, lane z).

The 97 Kd protein from HIAP-II appears most significant because the majority of patients with autoimmune disease reacted with a similar-sized protein in HIAP-I immunoblots, and some (2/10) HIV$^+$(gag-reactive) sera also reacted with this protein. This HIAP-II protein thus appears to contain an epitope which is cross-reactive with both an HIAP-I and an HIV protein. A monospecific rabbit antibody to p24$^{gag}$ from HIV-1 also reacts specifically with this HIAP-II protein. Isolated reactivities to a single band (not p97) were present in only 2 of the 19 control sera.

Interestingly, 7/8 of the reactive patients were not from the traditional HIV risk groups. As expected, patients with systemic autoimmune diseases recognize proteins in both HIAP-I and HIAP-II preparations, indicating a significant cross-reactivity of the antigens of these intracisternal retroviruses.

7. DEPOSIT OF BIOLOGICAL MATERIALS

The following were deposited with the American Type Culture Collection (ATCC), 12301 Parklawn Drive, Rockville Md., on May 4, 1995, on Apr. 27, 1994, and on Feb. 9, 1996, respectively:

HIAP-II viral particles, having accession number VR-2503; RH9/CB, a cell line comprising HIAP-II, having accession number CRL 11622; and RH9, a cell line having accession number CRL 12043.

Various publications are cited herein, the entire disclosures of which are incorporated herein, in their entirety, by reference. Citation of these references is not to be construed as an admission that these references are available as prior art against Applicants.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed:

1. A substantially purified human retrovirus associated with idiopathic CD4+ T-lymphocytopenia, having an icosahedral shape, smooth external surface, and a size of about 60 nm, prepared by a method comprising:
    (a) obtaining cells taken from a person suffering from idiopathic CD4+ T-lymphocytopenia;
    (b) adding the cells obtained in step (a), or an extract obtained therefrom, to a culture of RH9 cells having ATCC accession number CRL 12043;
    (c) culturing the RH9 cells with the cells obtained in step (a), or with the extract obtained therefrom, according to step (b);
    (d) lysing the cells of step (c) and preparing a microsomal fraction therefrom;
    (e) treating the microsomal fraction with detergent;
    (f) layering the detergent-treated microsomal fraction over a 48% (w/v) sucrose cushion;
    (g) centrifuging the microsomal fraction layered over the sucrose cushion at about 60,000 g for about 30 min to form pelletted material;
    (h) layering the pelletted material on a 33–68% (w/v) sucrose gradient;
    (i) centrifuging the sucrose gradient at about 100,000 g for about 12 hours; and
    (j) collecting fractions corresponding to a density of about 1.2 g/cm$^3$.

2. The substantially purified human retrovirus of claim 1, in which the cells taken from the person are peripheral blood mononuclear cells.

3. An isolated HIAP-II viral particle having ATCC accession number VR-2503.

4. A method of preparing a retrovirus associated with idiopathic CD4+ T-lymphocytopenia (ICL), having an icosahedral shape, a smooth external surface, and a size of about 60 nm, comprising:
    (a) obtaining cells taken from a person suffering from ICL;
    (b) adding the cells obtained in step (a), or an extract therefrom, to a culture of RH9 cells having ATCC accession number CRL 12043;
    (c) culturing the RH9 cells with the cells obtained in step (a), or with the extract obtained therefrom, according to step (b);
    (d) lysing the cells of step (c) and preparing a microsomal fraction therefrom;
    (e) treating the microsomal fraction with detergent;
    (f) layering the detergent-treated microsomal fraction over a 48% (w/v) sucrose cushion;
    (g) centrifuging the microsomal fraction layered over the sucrose cushion at about 60,000 g for about 30 min to form pelletted material;
    (h) layering the pelletted material on a 33–68% (w/v) sucrose gradient;
    (i) centrifuging the sucrose gradient at about 100,000 g for about 12 hours; and
    (j) collecting fractions corresponding to a density of about 1.2 g/cm$^3$.

5. The method according to claim 4, in which the cells taken from the person are peripheral blood mononuclear cells.

* * * * *